United States Patent
Morrison et al.

(10) Patent No.: US 8,653,154 B2
(45) Date of Patent: Feb. 18, 2014

(54) SYNERGISTIC EFFECTS OF BLENDING MULTIPLE ADDITIVES IN UHMWPE

(75) Inventors: Mark L. Morrison, Memphis, TN (US); Vivek D. Pawar, Germantown, TN (US); Lorenz Brunner, Zurich (CH); Shilesh C. Jani, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/318,731

(22) PCT Filed: May 4, 2010

(86) PCT No.: PCT/US2010/033494
§ 371 (c)(1),
(2), (4) Date: Nov. 3, 2011

(87) PCT Pub. No.: WO2010/129514
PCT Pub. Date: Nov. 11, 2010

(65) Prior Publication Data
US 2012/0046380 A1    Feb. 23, 2012

Related U.S. Application Data

(60) Provisional application No. 61/175,308, filed on May 4, 2009.

(51) Int. Cl.
| | | |
|---|---|---|
| G03G 9/097 | (2006.01) |
| B41M 7/00 | (2006.01) |
| A61L 2/08 | (2006.01) |
| C08F 2/46 | (2006.01) |
| C08G 61/04 | (2006.01) |

(52) U.S. Cl.
USPC ............. 522/75; 522/74; 522/71; 522/189; 522/1; 520/1

(58) Field of Classification Search
USPC .................. 522/75, 74, 71, 189, 1; 520/1
See application file for complete search history.

(56) References Cited

U.S. PATENT DOCUMENTS

| 6,277,390 B1 | 8/2001 | Schaffner |
| 2007/0059334 A1 | 3/2007 | Abt et al. |
| 2008/0215142 A1* | 9/2008 | Muratoglu et al. .......... 623/1.49 |
| 2009/0030524 A1 | 1/2009 | Schroeder et al. |

FOREIGN PATENT DOCUMENTS

| WO | WO 2008/006890 A2 | 1/2008 |
| WO | WO 2008/101134 A1 | 8/2008 |
| WO | WO 2008/113388 A1 | 9/2008 |

OTHER PUBLICATIONS

International Search Report, International Application No. PCT/US2010/033494, 4 pages.
Search Report; Chinese Patent Application No. 201080031064.8; May 31, 2013; 6 pages.
First Office Action; Chinese Patent Application No. 201080031064.8; Jun. 19, 2013; 15 pages.

* cited by examiner

*Primary Examiner* — Ling Choi
*Assistant Examiner* — Jessica E Whiteley
(74) *Attorney, Agent, or Firm* — Krieg DeVault LLP

(57) ABSTRACT

Oxidation resistant crosslinked ultrahigh molecular weight polyethylene (UHMWPE) is described, wherein at least two different additives in the manufacture synergistically increase the oxidation resistance of crosslinked UHMWPE. This allows the manufacture of oxidation resistant crosslinked UHMWPE using lower levels of additives and/or lower levels of crosslinking irradiation or chemicals. The lower levels of additives and/or crosslinking produce crosslinked UHMWPE having desired physical properties not possible without the synergistic interaction of the additives. This crosslinked UHMWPE may be used in medical prostheses such as in bearing components having desired physical properties such as wear resistance and oxidation resistance not possible without the synergistic interaction of the additives.

29 Claims, 4 Drawing Sheets

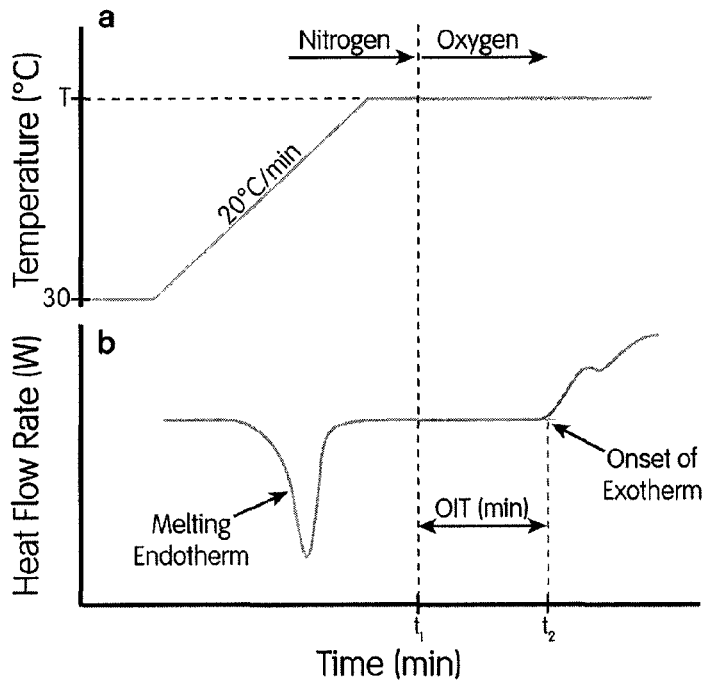
FIGS. 3 a and 3 b

SYNERGISTIC EFFECTS OF BLENDING MULTIPLE ADDITIVES IN UHMWPE

CROSS-REFERENCE TO RELATED APPLICATIONS

This is a U.S. National Stage filing of PCT/US2010/033494 (WO 2010/129514), International Filing Date 4 May, 2010, to which priority is claimed, and priority is claimed to U.S. Provisional Application 61/175,308, filed May 4, 2009, that is a priority application to PCT/US2010/033494. Both PCT/US2010/033494 and U.S. Provisional Application 61/175,308 are incorporated herein by reference in their entireties.

TECHNICAL FIELD OF THE INVENTION

The present invention relates to oxidation resistant polymers, including their manufacture and use. This includes as a nonlimiting example oxidation resistant crosslinked ultra-high molecular weight polyethylene (UHMWPE). This invention further relates to the use of polymers, including oxidation resistant crosslinked UHMWPE, in artificial body members, including medical prosthesis containing or made from one or more of such polymers. Nonlimiting examples include medical prostheses for replacing joints, such as hip and knee joints, wherein a polymer, such as oxidation resistant UHMWPE forms a bearing part of the joint, including providing a surface for articulating members of the joint. In a nonlimiting example, one portion of a medical prosthesis contains a polymer bearing that forms a surface, such as an acetabular surface, against which another portion of the medical prosthesis, such as a ball-like portion made of metal or ceramic, articulates against the bearing surface during use of the joint in a body.

BACKGROUND OF THE INVENTION

Prosthetic implants in arthroplasty, such as artificial knee and hip implants, typically involve the articulation of either a metal or ceramic ball shaped component, which is typically part of one half of a joint, against a polymer, such as UHMWPE, which is typically the other half of a joint, and is in the shape of a concave receptacle for receiving the articulation of the ball shaped component. More than a decade ago, it was discovered that exposure of the UHMWPE to ionizing radiation crosslinks the material and results in dramatically improved wear resistance. In contrast, the ionizing radiation also results in chain scission of the polymer chains and the creation of long-lived free radicals in the material. If these free radicals are not extinguished, they react with oxygen and result in oxidation of the polymer and subsequent degradation of the mechanical and tribological properties. To extinguish the free radicals, a post-irradiation heat treatment is commonly conducted.

Heating the crosslinked polymer above the melting temperature (i.e., re-melting) has been shown to extinguish all of the measurable free radicals in the crosslinked material and stabilize it against oxidation. On the other hand, re-melting also results in a decrease in crystallinity because the reduced mobility of the crosslinked chains inhibits the folding of the chains into crystalline lamella, which results in decreased yield and ultimate tensile strengths.

Alternatively, the crosslinked polymer can be heated to a temperature below the melting temperature (i.e., sub-melt annealing). Because the larger crystalline lamella are not melted during sub-melt annealing, the crystallinity is typically either maintained or increased, which typically maintains or improves the yield strength and leads to less of a decease in the ultimate tensile strength of the resultant material. In contrast, the choice of a sub-melt heat treatment leaves a measurable amount of free radicals in the unmelted crystalline regions of the material that can migrate out and oxidize with time.

As a result of these trade-offs, a method of stabilizing the highly crosslinked UHMWPE against oxidation without compromising the mechanical properties is desirable.

The blending of a UHMWPE resin with an antioxidant has been used to negate the need for a post-irradiation heat treatment and the subsequent trade-offs inherent to those methods. This approach blends a single antioxidant with the resin, and the blend is then consolidated by standard techniques, such as by compression molding or ram extrusion. This consolidated blend is then exposed to ionizing radiation to crosslink the material and improve the wear resistance. The blended antioxidant operates as a free-radical scavenger and interrupts the oxidation pathway by readily donating a hydrogen (H) atom to the damaged polymer chain and, in turn, taking on the free radical to form a stable free radical that it does not react with oxygen. Because a post-irradiation heat treatment may not be necessary for the removal of free radicals with this particular method, the mechanical properties are not degraded to the same extent.

On the other hand, there are two problems inherent to this blending method. First, each antioxidant molecule is capable of donating a finite number of hydrogen atoms/quenching or extinguishing a finite number of free radicals. For example, it has been theorized that each vitamin E molecule is capable of quenching two free radicals. As a result, the consumption of the antioxidant during the scavenging of free radicals could limit the effective time of protection against oxidation. For example, if the concentration of the antioxidant is too low, all of the free-radical-quenching ability could be consumed prior to the extinguishing of all of the free radicals, which would result in remaining free radicals that could react with oxygen and cause oxidation. From this prospective, it is preferable to have a high concentration of antioxidant to insure that all of it is not consumed prior to the capture of all of the free radicals and to maximize the long-term oxidation resistance. On the other hand, increasing the concentration of the antioxidant beyond a certain limit can result in a supersaturation that can cause elution or diffusion of the antioxidant out of the polyethylene. The result of this elution could be undesirable interactions of the antioxidant with the human body or depletion of the antioxidant remaining at the surfaces of the material.

Second, the improved wear resistance of the irradiated polymer is dependent upon the generation of free radicals by ionizing radiation and the subsequent combination of the free radicals to form chemical bonds (i.e., crosslinks) between polymer chains. The presence of an antioxidant during irradiation scavenges some of these free radicals and results in an undesired inhibition of crosslinking. As a result, higher irradiation doses are necessary to produce an equivalent level of wear resistance compared to an antioxidant-free polymer. As a consequence of increasing the irradiation dose to overcome the inhibition of crosslinking, the ductility and the toughness of the crosslinked material decrease even further. From this prospective, it is preferable to minimize the concentration of antioxidant to minimize the inhibition of crosslinking and the necessary irradiation dose to achieve a given wear resistance.

U.S. Pat. Nos. 7,431,874 and 7,498,365, each patent herein incorporated by reference, disclose a method to avoid these problems with blending. According to this method, the UHMWPE is consolidated and irradiated prior to the introduction of vitamin E (Vit E) into the material through diffusion. Because the material does not contain an antioxidant at the time of irradiation, there is no inhibition of crosslinking. Because inhibition is not a concern, the concentration of Vit E in the polymer can be increased to insure that there is a more than adequate amount of antioxidant to quench all of the existing free radicals and provide long-term oxidation resistance.

The negative aspects of this diffusion method are related to the time and expense necessary to diffuse a sufficient quantity of Vit E into the material and homogenize the concentration throughout the component. In addition, the higher concentrations of Vit E typically utilized in this process lead to a large concentration gradient, which could result in elution or diffusion of the Vit E out of the polyethylene and depletion of the antioxidant at the surface.

The combination of synergistic antioxidants and their effects on free-radical quenching and antioxidant "regeneration" or "recycling" has been considered in the past, but never related to medical uses, including in medical prostheses. For example, it has been demonstrated in the literature that the regeneration of Vit E takes place in vivo through chemical reactions with other molecules such as ascorbic acid (vitamin C). As a result of this interaction, the Vit E molecule is "recharged" and can theoretically quench 2 more free radicals. This process could proceed ad infinitum to provide long-term oxidation resistance with a low concentration of an antioxidant. Similar in-vivo regeneration of curcumin by a synergistic molecule has been theorized based on oncology research. In the polymeric sciences, the combinations of Vit E with a phosphate antioxidant or Vit E with polyhydric alcohol both reduce changes in color and promote higher retention of the Vit E during melt processing of polypropylene through a similar synergistic mechanism.

All of the efforts in the prior art related to UHMWPE have been to blend only one antioxidant into the UHMWPE. Moreover, EP Published Patent Application No. EP2047823 A1, for example, specifically states that "one antioxidant is preferred" for "economical and efficiency sake." The problem with the incorporation of a single antioxidant is that it is at least partially consumed during processing, during the quenching of free radicals after processing and during use/service. As a result, the prior art composition requires a higher concentration of antioxidant to insure that there is enough antioxidant to protect the medical device against long-term oxidation for the duration of the service life. This need for a higher concentration of a single antioxidant also results in inhibition of crosslinking, the need for higher irradiation doses to achieve a given wear resistance and, ultimately, leads to degraded mechanical properties.

BRIEF SUMMARY OF THE INVENTION

The present invention relates to the discovery that adding two or more additives to crosslinked UHMWPE improves the oxidation resistance of the material more than the additive effect of the two additives alone (i.e., synergistically). This discovery relates to at least the process of preparing oxidation resistant UHMWPE by adding two or more different antioxidants or additives to UHMWPE, medical prostheses made using this oxidation resistant UHMWPE, and the use of such medical prostheses in patients in need of such medical prostheses.

Examples of several potential processing routes for the invention are shown in FIG. 1. The invention includes a composition of a medical device in which combinations of select additives and/or antioxidants solve one or both of the aforementioned problems currently associated with the blending of a single antioxidant and inadequate crosslinking that can deteriorate the tribological performance of UHMWPE.

The invention includes blending of select, synergistic additives/antioxidants with another antioxidant into UHMWPE to regenerate or recycle the antioxidant and avoid the consumption of the antioxidant during free-radical scavenging, which would also permit the production of a medical device with lower concentrations of antioxidants that not only achieves higher oxidation resistance but also produces a highly wear-resistance surface. Furthermore, a lower concentration of antioxidant could lead to less inhibition of crosslinking upon exposure to radiation, which reduces the need for higher irradiation doses to achieve a given wear resistance and, in turn, leads to less degradation of the mechanical properties. Alternatively, this invention has improved oxidation resistance in comparison to prior devices even though it has a similar concentration of antioxidants.

Additionally, this invention has an advantage over the prior art in that the preservation of the antioxidant during consolidation/processing as well as a reduction of changes in UHMWPE color during processing and/or service.

One embodiment of the present invention comprises a process for preparing crosslinked oxidation resistant UHMWPE for use in medical prostheses comprising the steps of: (i) obtaining UHMWPE resin; (ii) combining the UHMWPE resin with both a first amount of a first additive and a second amount of a second additive, wherein the first and the second additives are different additives; (iii) consolidating the UHMWPE that has been combined with the first and second additives; and (iv) crosslinking the consolidated UHMWPE to create oxidation resistant UHMWPE.

In certain embodiments, the UHMWPE resin is crosslinked, for example by irradiation or chemical crosslinking, prior to being combined with the at least first and/or second additives.

In certain embodiments, the crosslinking of the UHMWPE is by irradiation crosslinking or by chemical crosslinking.

In still further embodiments of the invention, the synergistic effect on oxidation resistance by the combination of at least a first and at least a second additive allows for the amount of the first and/or the second additives to be lowered to achieve, for example, the same level of oxidation resistance as would have been achieved by a higher concentration of either additive alone.

Still further, in certain embodiments, due to the lower amount of the at least first and/or at least second additive in the UHMWPE, the dose of irradiation or chemical crosslinking can be reduced compared to what would be required if a single additive were present, because the lower concentration of antioxidant additives in the UHMWPE of the invention allows crosslinking at a lower dose as there are fewer additives to interfere with crosslinking.

In additional embodiments of the invention, the amount of the first additive that is combined with the UHMWPE resin in step (ii) (above) is about 50 ppm to about 5,000 ppm, more preferably about 50 ppm to about 2,000 ppm, still more preferably about 100 ppm to about 1,000 ppm, and further preferably about 200 ppm to about 800 ppm, based on the relative amount of the UHMWPE, and the amount of the second additive that is combined with the UHMWPE resin in step (ii) (above) is about 50 ppm to about 5,000 ppm, more preferably about 50 ppm to about 2,000 ppm, still more preferably about 100 ppm to about 1,000 ppm, and further preferably about 200 ppm to about 800 ppm, based on the relative amount of the UHMWPE.

In other embodiments of the invention, the amount of the first additive that is combined with the UHMWPE resin in step (ii) (above) is about 0.005 wt. % to about 0.5 wt. %, based on the relative amount of the UHMWPE, and the amount of the second additive that is combined with the UHMWPE in step (ii) is about 0.005 wt. % to about 0.5 wt. %, based on the relative amount of the UHMWPE.

More particularly, in certain embodiments where the crosslinking is done by irradiation, the dose of the crosslinking is about 1.5 MRad to about 30 MRad, more preferably about 2.5 MRad to about 15 MRad, and more preferably still about 2.5 MRad to about 12 MRad.

In other embodiments, after the oxidation resistant UHMWPE has been made as described above (combined with two or more additives, consolidated, and crosslinked), it is further machined into a bearing component for use in a medical prosthesis.

In certain embodiments, the crosslink densities of the combined, consolidated, and crosslinked UHMWPE, as well as that of a bearing component made from such are about 0.03 mol/dm$^3$ to about 0.50 mol/dm$^3$.

In more embodiments, including in those discussed above, the first additive is selected from the group consisting of phenolic antioxidants and hindered amines, and the second additive is selected from the group consisting of phosphorous additives, polyhydric alcohols, phenolic antioxidants, hindered amines, carotenoids, amino-acid-based additives, thiosynergists, and acid antioxidants.

Still further, in embodiments including those discussed above, the phenolic antioxidants of the first additive are selected from the group consisting of tocopherols, tocotrienols, curcuminoids, flavonoids, phenylpropanoids, and synthetic phenolic antioxidants; the hindered amine antioxidants of the first additive are selected from the group consisting of chimassorb 944, chimassorb 119 FL, cyasorb UV 3346, tinuvin 144, tinuvin 765, tinuvin 770 DF; the phosphorous additives of the second additive are selected from the group consisting of phosphites, phosphonites, and phosphines; the polyhydric alcohols of the second additive are selected from the group consisting of dipentaerythritol, tripentaerythritol, and trimethylolpropane ethoxylate; the phenolic antioxidants of the second additive are selected from the group consisting of tocopherols, tocotrienols, curcuminoids, flavonoids, phenylpropanoids synthetic antioxidants, and benzoquinols; the hindered amines of the second additive are selected from the group consisting of chimassorb 944, chimassorb 119 FL, cyasorb UV 3346, tinuvin 144, tinuvin 765, tinuvin 770 DF; the carotenoids of the second additive are selected from the group consisting of beta-carotene, lycopene, lutein, zeaxanthin, echinenone, and zeaxanthin; the amino-acid-based additives of the second additive are selected from the group consisting of glutathione, cystein, tyrosine, and tryptophan; the thiosynergists of the second additive are selected from the group consisting of distearyl thiodipropionate, irganox PS 800, and irganox PS 802; and the acid antioxidants of the second additive are selected from the group consisting of ascorbyl palmitate, ascorbate, and lipoic acid.

Still further, in embodiments of the invention, including for example those nonlimiting examples discussed above, the tocopherols of the first additive are selected from the group consisting of dl-alpha-tocopherol, alpha-tocopherol, delta-tocopherol, gamma-tocopherol, and beta-tocopherol; the tocotrienols of the first additive are selected from the group consisting of alpha-tocotrienol, beta-tocotrienol, gamma-tocotrienol, and delta-tocotrienol; the curcuminoids of first additive are selected from the group consisting of curcumin, demethoxycurcumin, bisdemethoxycurcumin, tetrahydrocurcumin, hexahydrocurcumin, curcumin sulphate, curcumin-glucuronide, hexahydrocurcumin, and cyclocurcumin; the flavonoids of the first additive are selected from the group consisting of naringenin, quercetin, hesperitin, luteolin, catechins, anthocyanins; the phenylpropanoid of the first additive is eugenol; the synthetic phenolic antioxidants of the first additive are selected from the group consisting of irganox 1010, irganox 1076, irganox 245, butylated hydroxytolunene, and butylated hydroxyanisole; the phosphites of the second additive are selected from the group consisting of ultranox U626, hostanox PAR24, irgafos 168, Weston 619, and irgafox 126; the phosphonate of the second additive is sandostab P-EPQ; the phosphine of the second additive is pepfine; the tocopherols of the second additive are selected from the group consisting of dl-alpha-tocopherol, alpha-tocopherol, delta-tocopherol, gamma-tocopherol, and beta-tocopherol; the tocotrienols of the second additive are selected from the group consisting of alpha-tocotrienol, beta-tocotrienol, gamma-tocotrienol, and delta-tocotrienol; the curcuminoids of second additive are selected from the group consisting of curcumin, demethoxycurcumin, bisdemethoxycurcumin, tetrahydrocurcumin, hexahydrocurcumin, curcumin sulphate, curcumin-glucuronide, hexahydrocurcumin, and cyclocurcumin; the flavonoids of the second additive are selected from the group consisting of naringenin, quercetin, hesperitin, luteolin, catechins, and anthocyanins; the synthetic antioxidants of the first additive are selected from the group consisting of irganox 1010, irganox 1076, irganox 245, butylated hydroxytoluene, and butylated hydroxyanisole; and the benzoquinol of the second additive is selected from the group consisting of ubiquinol and coenzyme Q10.

Additionally, in embodiments of the invention, including for example those discussed above, the catechins of the first additive are selected from the group consisting of epigallocatechin gallate, epigallocatechin, epicatechin gallate and epicatechin; the anthocyanins of the first additive are selected from the group consisting of cyanidin, delphinidin, malvidin, peonidin, petunidin, and pelargonidin; the catechins of the second additive are selected from the group consisting of epigallocatechin gallate, epigallocatechin, epicatechin gallate and epicatechin; and the anthocyanins of the second additive are selected from the group consisting of cyanidin, delphinidin, malvidin, peonidin, petunidin, and pelargonidin.

In preferred embodiments, the oxidation resistant UHMWPE is made according to the embodiments described above, including combining a first and a second additive with UHMWPE resin, consolidating the combined material, and crosslinking the consolidated UHMWPE, the first additive is a phenolic antioxidant and the second additive is a curcuminoid. Still further, preferred embodiments include the above described wherein the first additive is dl-alpha-tocopherol and the second additive is curcumin.

In still other preferred embodiments, the oxidation resistant UHMWPE is made according to the embodiments described above, including combining a first and a second additive with UHMWPE resin, consolidating the combined material, and crosslinking the consolidated UHMWPE, the first additive is a phenolic antioxidant and the second additive is a curcuminoid. Still further, preferred embodiments include the above described method wherein the first additive is dl-alpha-tocopherol and the second additive is curcumin. In other preferred embodiments further to those described above, the first additive is dl-alpha-tocopherol and the second additive is dipentaerythritol. In still further preferred embodiments, in the above embodiments, the first additive is curcumin and the second additive is dipentaerythritol.

In still further preferred embodiments, the UHMWPE resin and the first and second additives are combined as described above, the combination is consolidated as described herein, and the UHMWPE is irradiated, and wherein the first additive is dl-alpha-tocopherol and it is combined with the UHMWPE resin at about 250 ppm, based on the relative amount of the UHMWPE and the second additive is curcumin and it is combined with the UHMWPE at about 250 ppm, based on the relative amount of the UHMWPE, and the consolidated UHMWPE is crosslinked by irradiation at a dose of about 10 MRad.

In other preferred embodiments, the UHMWPE resin and the first and second additives are combined as described above, wherein the first additive dl-alpha-tocopherol is combined with the UHMWPE at about 300 ppm, based on the relative amount of the UHMWPE; the second additive curcumin is combined with the UHMWPE at about 300 ppm, based on the relative amount of the UHMWPE; and the crosslinking is by irradiation at a dose of about 10 MRad.

In still other preferred embodiments, the oxidation resistant UHMWPE is made according to the embodiments described above, including combining a first and a second additive with UHMWPE resin, consolidating the combined material, and crosslinking the consolidated UHMWPE, the first additive is curcumin and the second additive is a dipentaerythritol.

In still further preferred embodiments, the UHMWPE resin and the first and second additives are combined as described above, the combination is consolidated as described herein, and the UHMWPE is irradiated, and wherein the first additive is curcumin and it is combined with the UHMWPE resin at about 300 ppm, based on the relative amount of the UHMWPE and the second additive is dipentaerythritol and it is combined with the UHMWPE at about 300 ppm, based on the relative amount of the UHMWPE, and the consolidated UHMWPE is crosslinked by irradiation at a dose of about 10 MRad.

In other preferred embodiments, the UHMWPE resin and the first and second additives are combined as described above, wherein the first additive dl-alpha-tocopherol is combined with the UHMWPE at about 300 ppm, based on the relative amount of the UHMWPE; the second additive curcumin is combined with the UHMWPE at about 300 ppm, based on the relative amount of the UHMWPE; and the crosslinking is by irradiation at a dose of about 10 MRad.

Other preferred embodiments of the invention include a medical prosthesis comprising a bearing component comprising crosslinked UHMWPE made by any of the processes of making oxidation resistant UHMWPE summarized above and described in detail below. Moreover, in preferred embodiments, the medical prosthesis having the bearing made according to the processes of this invention may be a joint prosthesis, such as but not limited to a hip, knee, or finger joint prosthesis.

In other embodiments of the present invention, medical prostheses having bearing components of crosslinked oxidation resistant UHMWPE made according to the methods summarized above and described in detail below, can be administered to patients in need of such prostheses, including artificial hip and joint prosthetics.

In other embodiments of the present invention, the first and/or second additives are added to the UHMWPE in manners other than strictly by combining them with UHMWPE resin prior to consolidation and irradiation.

For example, in embodiment of the invention, a first antioxidant is combined with UHMWPE resin (that itself may have previously been crosslinked), and consolidated to produce consolidated UHMWPE having the first additive. The consolidated perform may then be crosslinked at this point, or after the next step of adding the second additive to the consolidated UHMWPE. In this step of this embodiment, the second additive is added to the consolidated UHMWPE (that has or has not been crosslinked) by diffusion. For example, the diffusion may be by immersion of the consolidated UHMWPE in a solution containing the second additive for a time sufficient for the second additive to enter the consolidated UHMWPE to the desired amount. The second additive may also be diffused into the consolidated UHMWPE by exposure to the consolidated UHMWPE to gas containing the second additive or to the second additive in a solid form, such as a fine powder uniformly laid on the UHMWPE and heated to allow diffusion of the second additive to a desired level. All other means of adding at least a first and a second additives to UHMWPE to produce crosslinked UHMWPE to which a first and a second additive have been added and in which the combination of the additives produce a synergistic increase in the oxidation resistance of the crosslinked UHMWPE are understood by one of skill in the relevant art to be within the scope of this invention.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIG. 3a is an illustration that each OIT experiment was begun with an isothermal segment at 30° C. for 10 minutes with a nitrogen flow to purge oxygen from the chamber, and where the furnace and sample were then heated at 20° C./min to the hold temperature (T), and held for 10 minutes to allow the sample and furnace to achieve equilibrium.

FIG. 3b is an illustration of oxidation-induction-time (OIT) measurements for the Examples showing the OIT measurement.

DETAILED DESCRIPTION OF THE EMBODIMENTS

Figure 1:
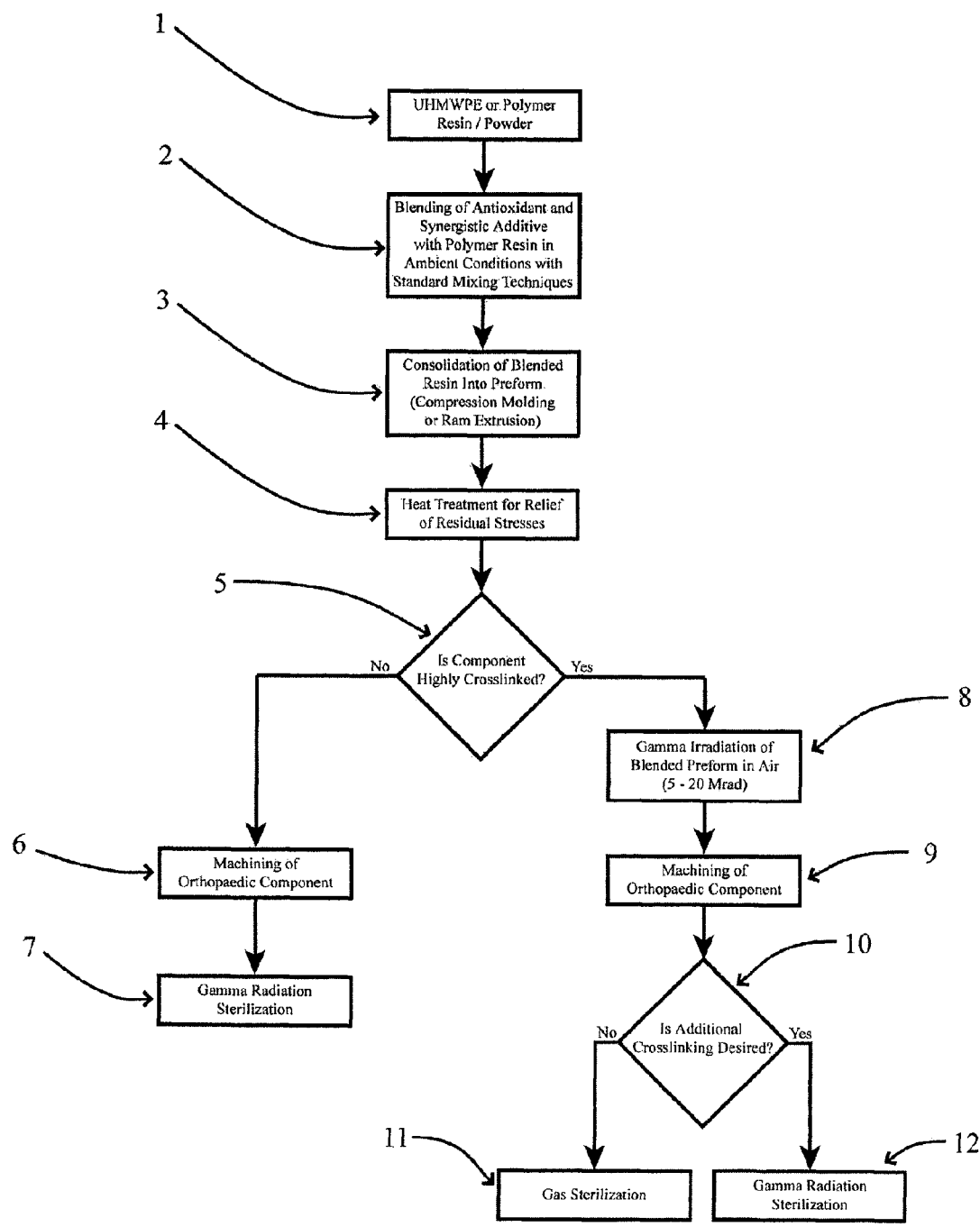
FIG. 1 is an example flowchart describing several potential processing routes.

The following description of the depicted embodiment(s) is merely exemplary in nature and is in no way intended to limit the invention, its application, or uses. It is readily apparent to one skilled in the art that various embodiments and modifications may be made to the present invention without departing from the scope and spirit of the invention.

The present invention relates to methods, products, and methods of using products related to crosslinked UHMWPE that has been combined with at least a first and at least a second antioxidant additive, wherein the combination of the first and the second antioxidant interact synergistically (i.e., in more than an additive manner) thereby allowing the creation of oxidation resistant crosslinked UHMWPE (XLPE) having improved wear and other properties. These properties make the inventive XLPE well suited for use in medical implants, although this is not a limitation on the claimed invention which relates to novel oxidation resistant XLPE generally. When used in medical prostheses, the XLPE may be in the form of a bearing, for example in a prosthetic joint. The oxidation resistant properties of the inventive XLPE make it well suited for use in an implant because its wear and other properties will not deteriorate over time because the XLPE is oxidation resistant. This includes that the product is not subject to oxidation during its manufacture and that the product does not oxidize over time. While not being bound or limited in any way by any theory, this long-term oxidation resistance appears to be a result of the XLPE containing at least some antioxidant additives, or products of such additives, including compounds and products formed by interactions of the additives and/or products of the additives in the UHMWPE.

Definitions

Unless defined otherwise, all terms, including technical and scientific terms, used herein have the same meaning as commonly understood by one of ordinary skill in the art to which this invention belongs. For purposes of the present invention, the following terms have the meanings given below unless otherwise indicated.

The term "ultrahigh molecular weight polyethylene" ("UHMWPE") is well known in the art, which meaning is adopted herein, and generally means polyethylene polymers having a weight average molecular weight of about 400,000 atomic mass units or more. Preferably, the ultrahigh molecular weight polyethylene has a weight average molecular weight of about 1,000,000, more preferably about 2,000,000, and most preferably about 3,000,000 atomic mass units or more. Typically, the weight average molecular weight of ultrahigh molecular weight polyethylene is less than about 10,000,000 atomic mass units, more preferably about 6,000,000 atomic mass units or less.

The term "medical prostheses" is well known in the art, which meaning is adopted herein, and generally means a device intended to replace or supplement part of an animal's musculoskeletal system. Common uses of medical prostheses within the scope of this invention include but are not limited to artificial joints, including for example hip, knee, shoulder, finger, elbow, ankle, facet, and jaw joints. As an example, but not a limitation, XLPE may be used in medical prostheses as a bearing component forming one part of a joint. For example, a UHMWPE bearing component in a prosthetic joint, such as a hip or knee joint, may be in the shape of receiving cup (such as an acetabular cup) which provides a surface against which another component of an artificial joint, such as a metal or ceramic ball, articulates in the movement of the joint. Other uses of UHMPE in medical prostheses are expressly within the scope of this invention.

As used herein, term "compound(s)" means anything capable of being defined, identified, quantified, etc. as a single substance, and is not limited to any more specific meaning unless clearly so-limited by the specific context of the use of the term. Therefore, the term "compound(s)" includes but is not limited to chemical compounds, entities, molecules, complexes, agents, additives, and the like. Further, for example, unless otherwise limited by the specific context of their use, the terms "antioxidant compound," "antioxidant additive," "antioxidant substance," and "antioxidant" mean the same thing.

"Combining," "combination," "mixing," "mixture," and the like have their ordinary meanings in the art and include but are not limited to placing two or more agents in physical proximity to one another by, for example, admixing, blending, diffusing, compressing, mingling, comingling, and the like. Moreover, unless the context expressly indicates otherwise, the term "combining," "combination," "mixing," "mixture" and the like as used herein include combining two or more agents in any order or sequence and in any amounts.

"Irradiate," "irradiating," "irradiated," and the like, as well as "radiate," "radiating," "radiated," and the like, have the meaning known in the relevant art and generally mean exposing an object (subject, article, etc.) to ionizing "radiation," wherein the object exposed to the ionizing "radiation" has been "irradiated," and include but are not limited to gamma radiation (or gamma irradiation), electron beam irradiation (or electro beam radiation), and including any dose of such irradiation (or irradiation), and in any sequence. Further, one of ordinary skill in the relevant art understands that while there are subtle differences between the meaning of the terms irradiation and radiation, for example as shown above (e.g., radiation is emitted from a source and the object receiving the radiation is irradiated), the terms are often used interchangeably in the relevant art to refer to the same thing and unless otherwise noted, this meaning is expressly adopted herein. Therefore, for a nonlimiting example, reference herein to an object that "has been irradiated" means the same thing as reference to an object that "has been radiated," or for a non-limiting example an object may be "irradiated" or "radiated," wherein both meaning the same thing, and so forth.

"Crosslinked," "crosslink" and "crosslinking," etc. in relation to crosslinked UHMPE (also known as "XLPE"), have the meaning known in the relevant art and generally mean the formation of chemical, covalent bonds between two or more polymeric chains so as to create a molecular network [e.g., 1]. "Crosslinked UHMWPE" (or "XLPE") may be made by crosslinking UHMWPE by any means including but not limited to by radiation or by chemical means. Radiation crosslinking of UHMWPE is well known in the art and generally involves the exposure of UHMWPE to ionizing radiation, such as but not limited to gamma radiation or an electron beam. The following examples are illustrative but not limiting. Mildly crosslinked UHMWPE materials can generally created during sterilization with a gamma-radiation dose in the range of 2.5 to 4.0 Mrad, which can be conducted as the last step of the process with the finished, cleaned and packaged implant. Highly crosslinked materials can be created through exposure to gamma radiation or an electron beam at doses greater than 4.0 Mrad. Consolidated bars or rods are typically exposed to radiation to create highly crosslinked UHMWPE. Within the scope and spirit of this invention, crosslinked UHMWPE may be made by crosslinking UHMWPE resin prior to consolidation or prior to combining and consolidation (and may optionally be additionally crosslinked again upon crosslinking (such as by radiation) of the consolidated UHMWPE and/or a shaped implant made from the consolidated UHMWPE). Chemical crosslinking is well known in the art and generally includes the blending of UHMWPE resin with a peroxide [see, e.g., 2] or silane [see, e.g., 4].

"Consolidate," and "consolidating" in the context of UHMWPE, such as "consolidating UHMWPE" have the meaning known in the art, and generally mean heating and compressing UHMWPE, which in the present invention may contain one or more agents, and ram extruding or compression molding the UHMWPE to form "consolidated UHMWPE" which is typically in the form of a bar or rod. The terms "consolidate" and "consolidated" in reference to UHMWPE generally include that the UHMWPE that has been heated and compressed and has also been treated by the conventional step, practiced in the relevant art (and well known to one of ordinary skill in the pertinent art), of annealing after consolidating (consolidation) to relieve stress in the consolidated UHMWPE, which annealing generally involves heating the UHMWPE for a determined time and temperature to release stress caused by the compression. Thus, the term "consolidated UHMWPE," as used herein includes UHMWPE that has been heated and compressed and shaped by ram extrusion or compression molding and subsequently annealed to relieve consolidating stress.

The term "dl-alpha-tocopherol", also known as all-rac-alpha-tocopherol, means synthetic vitamin E that is an all-racemic mixture of approximately equal amounts of the eight possible stereoisomers (i.e., alpha-tocopherol, beta-tocopherol, gamma-tocopherol, delta-tocopherol, alpha-tocotrienol, beta-tocotrienol, gamma-tocotrienol, and delta-tocotrienol) [see, e.g., 6]. The additive dl-alpha-tocopherol is commercially available, for example, from Sigma-Aldrich, St. Louis, Mo. (Item T3251).

The term "curcumin" refers to, in its most pure form the compound "1,7-bis(4-hydroxy-3-methoxyphenyl)-1,6-heptadiene-3,5-dione," also known as "diferuloymethane," that is isolated from tumeric (*Curcuma longa*) or has been chemically synthesized.

The term "butylated hydroxytoluene" may be abbreviated as "BHT."

The term "butylated hydroxyanisole" may be abbreviated as "BHA."

Synthetic antioxidant means man-made and not naturally found.

The term "synergism" has the meaning set forth below in the following 8 full paragraphs (including this paragraph) and the following equations (1)-(4). The term "synergism" is known in the art related to this invention to mean the cooperative interaction between two or more additives that enhances the stabilization of a polymer by more than the sum of their individual effects [see, e.g., 9]. This meaning is set forth in the formulae below. Additionally, for purposes of clarity, the art also recognizes antagonism, which is the interaction between two or more additives that degrades the stabilization of a polymer such that their combined effect is less than the sum of their individual effects. Further, the art recognizes that the balance between synergism and antagonism is an additive effect, wherein the combined effect of two additives is equivalent to the sum of their individual effects. These definitions are shown via the following non-limiting formulae:

If:
$r_a$=relative concentration of additive a in the combined UHMWPE,
$r_b$=relative concentration of additive b in the combined UHMWPE,
$r_n$=relative concentration of additive n in the combined UHMWPE,
where $r_a+r_b+\ldots +r_n=1$
$OIT_a$=Oxidation-induction time (OIT) of additive a alone in UHMWPE,
$OIT_b$=Oxidation-induction time (OIT) of additive b alone in UHMWPE,
$OIT_n$=Oxidation-induction time (OIT) of additive n alone in UHMWPE, and
$OIT_{a,b,\ldots n}$=Oxidation-induction time (OIT) of additives a, b, . . . n in UHMWPE $$\text{Additive Interaction: } OIT_{a,b,\ldots n}=r_a(OIT_a)+r_b(OIT_b)+\ldots +r_n(OIT_n) \tag{1}$$

$$\text{Synergistic Interaction: } OIT_{a,b,\ldots n}>r_a(OIT_a)+r_b(OIT_b)+\ldots +r_n(OIT_n) \tag{2}$$

$$\text{Antagonistic Interaction: } OIT_{a,b,\ldots n}<r_a(OIT_a)+r_b(OIT_b)+\ldots +r_n(OIT_n) \tag{3}$$

One of ordinary skill in the relevant art will readily understand that these and other specific equations for defining synergism apply in specific situations, and that it is well within the skill of one of ordinary skill in the relevant art to modify equations to create equations specific for defining synergism under various circumstances. For example, the above equations (1)-(3) apply when the sum of the concentrations of the additives in the combined UHMWPE together are equivalent to the concentrations of the additives in UHMWPE alone. One of ordinary skill in the art can readily define other equations to demonstrate synergism when this situation is not present.

As an example of this, one of the primary goals of the invention is to allow for a reduction in the concentration of the primary additive while simultaneously maintaining or improving the oxidation resistance of the combined, consolidated, and crosslinked UHMWPE. Therefore, one of ordinary skill in the relevant art would know that the aforementioned equations are well suited for demonstrating synergism in this particular case. However, it would be well within the skill of one of ordinary skill in the art to determine equations for this (or any) situation. For example, to define synergism under these specific circumstances, one skilled in the art would derive the following equation is a non-limiting example to define synergism between two or more additives:

If:
$r_a$=relative concentration of additive a in the combined UHMWPE,
$r_b$=relative concentration of additive b in the combined UHMWPE,
where: $r_a+r_b=1$
$C_a$=mass concentration of additive a alone in UHMWPE,
$C_b$=mass concentration of additive b alone in UHMWPE,
$OIT(C_a)$=Oxidation-induction time (OTT) of additive a alone at concentration $C_a$ in UHMWPE,
$OIT(C_b)$=Oxidation-induction time (OIT) of additive b alone at concentration $C_b$ in UHMWPE,
$OIT(C_a',C_b')$=Oxidation-induction time (OIT) of additive a at mass concentration $C_a'$ and additive b at mass concentration $C_b'$ in UHMWPE
where: $C_a'<C_a$,
$C_b'<C_b$, and
$C_a'+C_b'=C_a=C_b$ $$OIT(C_a',C_b')\geq r_a[OIT(C_a)]+r_b[OIT(C_b)] \tag{4}$$

Furthermore, it is known in the art that synergistic interaction between two or more stabilizing additives or compounds (also known as stabilizer(s)) can be classified as acting through one of the following mechanisms:
(1) Both additives react together to give a new species more efficient in stabilization;
(2) A "secondary" additive reacts with the "primary" one or its by-products to regenerate it or to inhibit deleterious effects; and
(3) Both additives act at distinct levels of the radical chain oxidation and the synergy results only from a kinetic effect.

While expressly not to be bound by theory or limited in any manner by theory, and solely for purposes of illustration, based upon studies in the literature, the inventors theorize that the addition of more than one additive to crosslinked UHMWPE acts through either mechanism 2 or 3 or both, depending upon the particular additives selected.

For example, previous studies have demonstrated that various additives such as vitamin C, catechins and polyhydric alcohols act through Mechanism 2 in combination with a phenolic antioxidant such as alpha-tocopherol. These compounds can regenerate or recycle the tocopheroxyl radical back into alpha-tocopherol and, therefore, return the molecule back to the original state. This, in turn, permits the alpha-tocopherol molecule to quench additional free radicals and continue protecting the material from oxidation.

Alternatively, phenolic antioxidants combined with sulphides or phosphites are generally believed to act through Mechanism 3, where the phenolic additives quench peroxide radicals and the sulphides or phosphites convert the hydroperoxide groups to alcohols.

Finally, some combinations of additives are believed to work through mechanisms 2 and 3 together. For example, in blends of alpha-tocopherol and the phospite Ultranox U626 in polypropylene, the phosphite has been reported to participate both in the deactivation of hydroperoxides (Mechanism 3) and in the regeneration of alpha-tocopherol (Mechanism 2).

The term "nominal" as used herein means the concentration of a substance to be combined with another substance (for example, an antioxidant additive to be combined with UHMWPE resin) wherein the amount of the substance to be combined with another substance is the amount of the substance before it is combined. For example, if a specific antioxidant additive is to be combined with a specific amount of UHMWPE, the "nominal" concentration of the specific antioxidant would be its amount immediately prior to combining (often, but not always or necessarily, expressed as a weight percentage of the substance into which it will be combined). This form of measurement is particularly useful where the substance being added to another substance may be consumed, combined, altered, reacted, or otherwise changes or become difficult to quantify once it is combined. However, the term "nominal" does not necessarily require that a "nominal" quantity of a substance combined with another substance change form or otherwise be difficult to measure and quantify once combined.

As used herein, the term "neat" refers to a substance that has had nothing added to it (i.e., without additives). For a non-limiting example, "neat GUR1020 UHMWPE" in the first line of Example 2 means that the GUR1020 UHMWPE has not had anything added to it at that point in the process (i.e., prior to combining to create Materials A, B, and/or C).

As used herein, the term "virgin" refers to a compound, combination, substance, object, and the like that has not been treated in an example as have been other aspects of the example, and generally refers to a control. For example, in Example 2, in the following sentence the term "virgin" means that the Neat GUR 1020 was not irradiated and is an unirradiated control: "Neat GUR1020 UHMWPE was consolidated, annealed to relieve residual stresses and remained in the unirradiated condition (Material D—virgin)."

The first and second additives in the present invention include but are expressly not limited to the following examples: (1) first additives: (a) phenolic antioxidants, including (i) tocopherols, including (1) dl-alpha-tocopherol, (2) alpha-tocopherol, (3) delta-tocopherol, (4) gamma-tocopherol, and (5) beta-tocopherol, (ii) tocotrienols, including (1) alpha-tocotrienol, (2) beta-tocotrienol, (3) gamma-tocotrienol, and (4) delta-tocotrienol, (iii) curcuminoids, including (1) curcumin (i.e., diferuloymethane), (2) demethoxycurcumin, (3) bisdemethoxycurcumin, (4) tetrahydrocurcumin, (5) hexahydrocurcumin, (6) curcumin sulphate, (7) curcumin-glucuronide, (8) hexahydrocurcuminol, and (9) cyclocurcumin, (iv) flavonoids, including (1) naringenin, (2) quercetin, (3) hesperitin, (4) luteolin, (5) catechins (including (a) epigallocatechin gallate, (b) epigallocatechin, (c) epicatechin gallate, and (d) epicatechin), (6) anthocyanins (including (a) cyanidin, (b) delphinidin, (c) malvidin, (d) peonidin, (e) petunidin, and (f) pelargonidin), (v) phenylpropanoids, including (1) eugenol, (vi) synthetic antioxidants, including (1) irganox 1010, (2) irganox 1076, (3) irganox 245, (4) butylated hydroxytoluene (BHT), and (5) butylated hydroxyanisole (BHA), and (b) hindered amines, including (i) chimassorb 944, (ii) chimassorb 119 FL, (iii) cyasorb UV 3346, (iv) tinuvin 144, (v) tinuvin 765, and (vi) tinuvin 770 DF; and (2) second additives: (a) phosphorous compounds, including (i) phosphites, including (1) ultranox U626, (2) hostanox PAR24, (3) irgafos 168, (4) irgafos 126, and (5) weston 619, (ii) phosphonites, including (1) sandostab P-EPQ, (iii) phosphines, including (1) PEPFINE, (b) polyhydric alcohols, including (i) dipentaerythritol, (ii) tripentaerythritol, (iii) trimethylolpropane ethoxylate, (c) phenolic antioxidants, including (i) tocopherols, including (1) dl-alpha-tocopherol, (2) alpha-tocopherol, (3) delta-tocopherol, (4) gamma-tocopherol, (5) beta-tocopherol, (ii) tocotrienols, including (1) alpha-tocotrienol, (2) beta-tocotrienol, (3) gamma-tocotrienol, and (4) delta-tocotrienol, (iii) curcuminoids, including (1) curcumin (i.e., diferuloymethane), (2) demethoxycurcumin, (3) bisdemethoxycurcumin, (4) tetrahydrocurcumin, (5) hexahydrocurcumin, (6) curcumin sulphate, (7) curcumin-glucuronide, (8) hexahydrocurcuminol, and (9) cyclocurcumin, (iv) flavonoids, including (1) naringenin, (2) quercetin, (3) hesperitin, (4) luteolin, (5) catechins (including (a) epigallocatechin gallate, (b) epigallocatechin, (c) epicatechin gallate, and (d) epicatechin), (6) anthocyanins (including (a) cyanidin, (b) delphinidin, (c) malvidin, (d) peonidin, (e) petunidin, and (f) pelargonidin), (v) phenylpropanoids, including (1) eugenol, (vi) synthetic antioxidants, including (1) irganox 1010, (2) irganox 1076, (3) irganox 245, (5) butylated hydroxytoluene (BHT), and (6) butylated hydroxyanisole (BHA), (vii) benzoquinols, including (1) ubiquinol, and (2) coenzyme Q10, (d) hindered amines, (i) chimassorb 944, (ii) chimassorb 119 FL, (iii) cyasorb UV 3346, (iv) tinuvin 144, (v) tinuvin 765, and (vi) tinuvin 770 DF, (e) carotenoids, including (i) beta-carotene, (ii) lycopene, (iii) lutein, (iv) zeaxanthin, (v) echinenone, and (iv) zeaxanthin, (f) amino-acid-based additives, including (i) glutathione, (ii) cystein, (iii) tyrosine, and (iv) tryptophan, (g) thiosynergists, including (i) distearyl thiodipropionate, (ii) irganox PS 800, (iii) irganox PS 802, and (h) other additives, including (i) ascorbate, (ii) ascorbyl palmitate, and (iii) lipoic acid.

One embodiment pertains to a bearing material for a medical device that contains at least two types of additives that produce a synergistic effect in scavenging of free radicals in a crosslinked polyethylene. The preferred antioxidant additives are Vit E and curcumin. Any other synthetic or natural antioxidants or synergistic additives can be used in combination to achieve such effect. For example, synergistic additives and antioxidants could include but are not limited to curcumin, Vit E, polyhydric alcohol, phosphites, ubiquinol-10, glutathione, ascorbic acid, anthralin, catechins such as epigallocatechin gallate, or flavonoids.

An antioxidant such as Vit E or curcumin is blended with a corresponding, synergistic additive or antioxidant and UHMWPE resin in known concentrations. This blend is consolidated through conventional techniques such as ram extrusion or compression molding. Following consolidation, the material may be subjected to a standard stress-relieving anneal to minimize residual stresses present in the material. The consolidated blend is exposed to ionizing radiation (e.g., gamma or electron beam radiation) in air or in an inert environment to crosslink the material to produce a desired wear resistance. Due to the presence of the antioxidant and additive, a post-irradiation heat treatment may not be necessary. A medical device, such as an orthopaedic bearing component, could then be machined from this highly crosslinked, consolidated blend and sterilized by conventional methods.

An alternative embodiment could include a medical device made of UHMWPE that is crosslinked to 10 Mrad with a preferred ratio of Vit E to curcumin of 1:1, but any other ratios could be used. The preferred radiation dose is from 1.5 Mrad to 30 Mrad.

Alternatively, one or more additives are blended with the resin and one or more of the synergistic additives are diffused using a high temperature process in the consolidated component after consolidation and either before or after crosslinking. For example, curcumin could be blended with the resin and consolidated into a preform. After crosslinking, vitamin E could be diffused into either the preform or the machined implant. The diffusion process could be conducted at room temperature. However, for greater diffusion depths, higher temperatures up to melting point of the polymer could be used. Thus, for example, for polyethylene, diffusion can be carried out at 150° C. In order to minimize the deformation of the preform, lower temperatures, for example 120° C., can be used. The antioxidant used for the diffusion process can be in solid, liquid or gaseous form. For solid form antioxidant, fine ground powder is uniformly laid on the preform and the whole assembly is heated to allow the antioxidant to diffuse. Alternatively, the solid antioxidant could be dissolved in a suitable solvent. For liquid form antioxidant such as alpha-tocopherol (vit E), the preform is soaked in the liquid solution at room temperature or at elevated temperature for a few hours to several hours. The soaking time can decided based on the diffusivity of the antioxidant in the polymer and the temperature used. Higher diffusivity will allow shorter diffusion times.

In an alternative embodiment, the crosslinking is achieved using a chemical crosslinking process known in the art. In such processes, one or more additives/antioxidants could be diffused or blended simultaneously during crosslinking along with the crosslinking agent. Alternatively, chemical crosslinking is done after the antioxidant(s)-blended resin is consolidated.

In some embodiments, the resin is mildly crosslinked and is then blended with the antioxidants. After consolidation, it is again irradiated to achieve the desired level of crosslinking.

Figure 2:
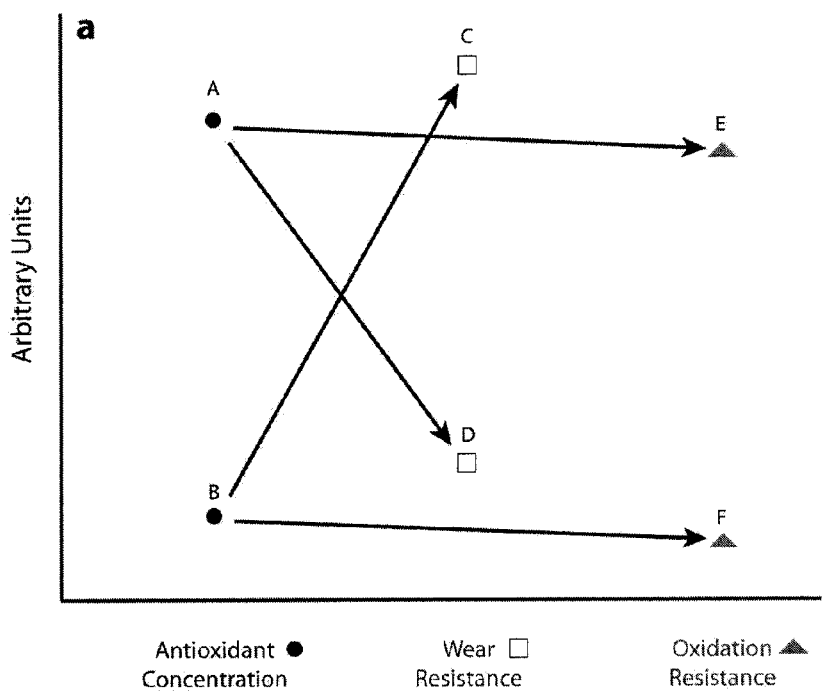
FIG. 2a is an illustration of the relationship of antioxidant concentration (●), wear resistance (□), and oxidation resistance (▲) in crosslinked UHMWPE having a single antioxidant additive.
FIG. 2b is an illustration of the relationship of antioxidant concentration (●), wear resistance (□), and oxidation resistance (▲) in crosslinked UHMWPE having at least a first and a second antioxidant additive.
Figure 2:
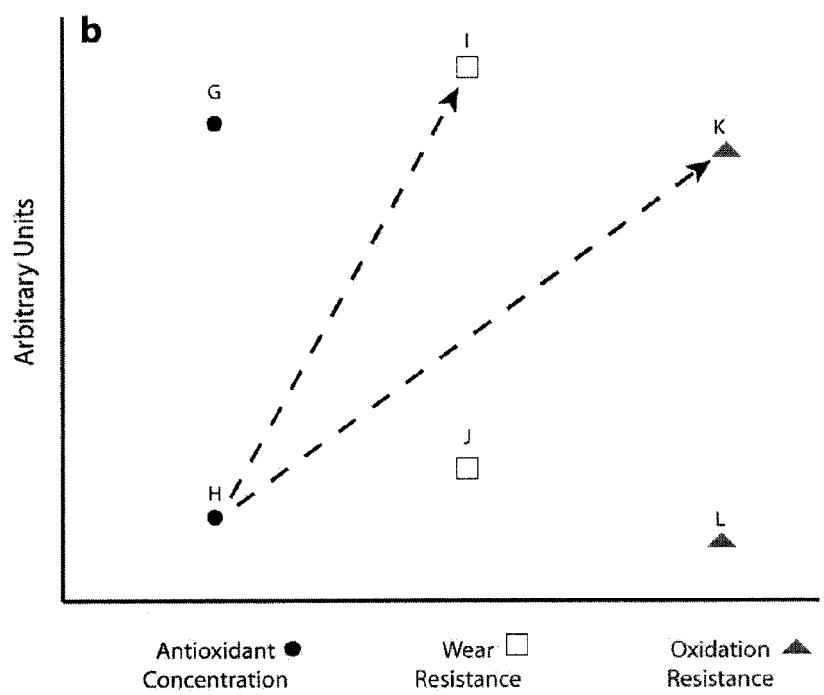

With the use of a single antioxidant in UHMWPE, the concentration must be carefully selected to balance both the wear resistance and the oxidation resistance with a given irradiation dose. As shown in FIG. 2 a, the selection of a high level of antioxidant (Point A) inhibits crosslinking to a greater extent, which results in decreased wear resistance (Point D). On the other hand, the higher concentration of the antioxidant provides for greater resistance to oxidation (Point E).

Since wear resistance is a primary metric of interest for crosslinked UHMWPE in orthopaedic devices, one could choose to use a lower concentration of the antioxidant (Point B), which would inhibit crosslinking to a lesser extent and provide improved wear resistance (Point C). However, the lower concentration of antioxidant available for the long-term stabilization of the device results in degraded resistance to oxidation (Point F).

The incorporation of a primary antioxidant with at least one secondary additive or antioxidant into the UHMWPE can change the relationships between these important metrics (FIG. 2 b). The interaction between the stabilizing compounds results in improved resistance to oxidation (Point K) at a lower concentration of the primary antioxidant (Point H). Because the primary antioxidant concentration is lower, the inhibition of crosslinking is less and a given irradiation dose results in higher wear resistance (Point I).

EXAMPLES

Example 1

Now referring to FIG. 1, Step 1 indicates the selection of the polymer resin or powder to be used as the starting material based upon the application and the required performance/properties. For example, the polymer resin could be GUR1050 or GUR1020 ultra-high molecular weight polyethylene (UHMWPE), Teflon, polyurethane, polyetheretherketone (PEEK), thermoplastic elastomers, etc. In Step 2, this selected polymer resin is combined with at least two synergistic additives by blending in ambient conditions with standard blending/mixing techniques such as planetary, ribbon, tumble, vertical, rotary, plow, cylindrical or blade blending. In certain cases low molecular-weight fractions of the polymer may be used to achieve uniform distribution of the antioxidant additives. The low molecular-weight fractions allow a lower melting point constituent that may allow diffusion of antioxidant and thus uniform dispersion. As an example, lower molecular-weight fraction polyethylene can be blended with ultra-high molecular weight polyethylene as a starting resin. In Step 3, the blend is consolidated into a preform through standard techniques such as compression molded, ram extrusion, injection molding, etc. In Step 4, a standard heat treatment is conducted to relieve residual stresses generated during consolidation. For example, a typical post-consolidation heat treatment for relief of residual stresses involves heating the consolidated material in an oven or appropriate liquid bath to 104° C. or above, holding at the soak temperature, and slowly cooling the material at a rate less than 6° C. per hour. Alternatively, heat treatment can be done using a convection-type heating oven that is heated using resistive heating elements. Alternatively, vacuum heating can be used. In Step 5, a decision is made depending on the level of crosslinking desired in the final implant. If the final implant is not intended to be highly crosslinked, Step 6 includes the machining of the desired orthopaedic component into the final shape. In Step 7, the implant is sterilized by gamma radiation with the standard dose of 2.5 to 4.0 Mrad (25 to 40 kGy). If the final implant is intended to be highly crosslinked, Step 8 describes the irradiation of a preform in air by gamma or electron-beam radiation in air with doses that range from 5 to 20 Mrad (50 to 200 kGy). In Step 9, the final implant is machined from the highly crosslinked, preform material. In Step 10, a decision is made as to the desired method of sterilization for the highly crosslinked implant. In Step 11, the implant is sterilized by gas sterilization without radiation. In Step 12, the final implant is sterilized by gamma radiation with the standard dose range of 2.5 to 4.0 Mrad (25 to 40 kGy).

Further referring to Example 1, and in a non-limiting manner, in one embodiment the implant can be used as a bearing material for hip arthroplasty; in one embodiment the implant can be used as a bearing material for knee arthroplasty; in one embodiment the implant can be used as a bearing material for spinal arthroplasty; and in one embodiment can be used as a bearing material for shoulder arthroplasty.

Example 2

Neat GUR1020 UHMWPE resin was combined with the following:
Material A—dl-alpha-tocopherol (vitamin E or Vit E) at a nominal concentration of 500 ppm (0.05 wt. %),
Material B—Purified curcumin, or diferuloymethane (97.7% by HPLC), at a nominal concentration of 500 ppm (0.05 wt. %),
Material C—dl-alpha-tocopherol and purified curcumin at nominal concentrations of 250 ppm (0.025 wt. %) each It should be noted that dl-alpha-tocopherol, also known as all-rac-alpha-tocopherol, refers to synthetic vitamin E that is an all-racemic mixture of approximately equal amounts of the eight possible stereoisomers (i.e., alpha-tocopherol, beta-tocopherol, gamma-tocopherol, delta-tocopherol, alpha-tocotrienol, beta-tocotrienol, gamma-tocotrienol, and delta-tocotrienol). These materials were then consolidated by compression-molding, annealed to relieve residual stresses, and subsequently gamma-irradiated with a nominal dose of 10 Mrad (100 kGy). Following irradiation, no heat treatments were conducted.

Two control materials were also evaluated. Neat GUR1020 UHMWPE was consolidated, annealed to relieve residual stresses and remained in the unirradiated condition (Material D—virgin). In addition, neat GUR1020 UHMWPE was consolidated, annealed to relieve residual stresses, gamma-irradiated with a nominal dose of 10 Mrad (100 kGy), and re-melted to stabilize the highly crosslinked material (Material E—10-XLPE).

To assess the oxidation resistances of these materials, oxidation-induction-time (OIT) experiments were conducted with a Netzsch 204 F 1 Phoenix (Huntersville, N.C.) Differential Scanning calorimeter (DSC) in a manner similar to that described in ASTM D3895-07. Plate-like samples were removed from the interiors of the materials, weighed to a resolution of 0.01 mg and ranged in mass from 9 to 11 mg. Each sample was crimped in an aluminum crucible, and a hole was punched in the lid to allow for gas flow. An empty aluminum crucible with a hole in the lid was used as the reference sample. Three samples were evaluated per material (n=3).

OIT experiments have been utilized to rapidly assess the oxidative stability of various polymers including a limited number of studies with UHMWPE. As shown in FIG. 3 *a*, each OIT experiment was begun with an isothermal segment at 30° C. for 10 minutes with a nitrogen flow rate of 50 mL/min. This step was utilized to purge oxygen from the chamber and the aluminum crucible holding the sample to avoid oxidation during heating. The furnace and sample were then heated at 20° C./min to the hold temperature (T), which was 190° C. in this experiment, and held for 10 minutes to allow the sample and furnace to achieve equilibrium (FIG. 3 *a*). At time $t_1$, the nitrogen gas flow was stopped, and an oxygen flow at 50 mL/min was immediately begun. The temperature of the furnace and the sample were held at T until an exothermic reaction was observed (FIG. 3 *b*), which signifies the occurrence of oxidation in the sample. The extrapolated onset time of this exotherm was determined to be $t_2$, and the OIT ($\tau$) was calculated as the difference between $t_1$ and $t_2$. The induction time observed for additive-stabilized polymers has traditionally been interpreted as the gradual consumption of the stabilizer, which is followed by an exothermic oxidation reaction that is measurable in the DSC (FIG. 3 *b*). As a result, a greater oxidation-induction time indicates a greater resistance to oxidation.

Figure 4:
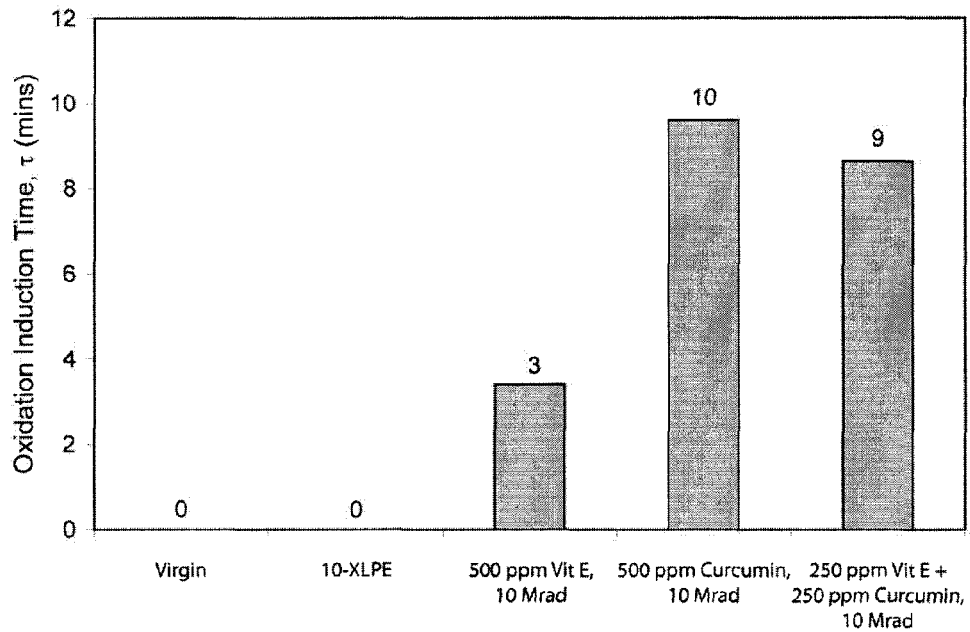
FIG. 4 shows the oxidation-induction-time (OIT) measurements for the samples of Example 2.

In this experiment, the standard control materials both exhibited oxidation-induction times of zero, which means that they oxidized immediately upon introduction of oxygen flow at this hold temperature (FIG. 4). In contrast, the highly crosslinked blend with 500 ppm Vit E (Material A) was found to exhibit an OIT of 3 mins, and the highly crosslinked blend with 500 ppm curcumin (Material B) had an OIT of 10 mins (FIG. 4). Based on the rule of mixtures (Equation 5) and the linear relationship between antioxidant concentration and induction time that is known in the art, one would expect an OIT of about 6.5 mins for a 1:1 blend of Vit E and curcumin (Material C).

$$OIT_{Mix} = 0.5(OIT_a + OIT_b) \tag{5}$$

Where: $OIT_{Mix}$ is the OIT for the mixture,
$OIT_a$ is the OIT for substance a in UHMWPE, and
$OIT_b$ is the OIT for substance b in UHMWPE.

However, the inventors have discovered that the blend with both Vit E and curcumin (Material C) resulted in an OIT of 9 mins (FIG. 4), which is 38% higher than might be expected, based upon Equation 5.

The mechanical properties of these materials were evaluated through uniaxial tensile and Izod impact testing. Uniaxial tensile testing was conducted according to ASTM D638-03. In these tests, Type IV samples with thicknesses of 3.0 mm were tested at 5.08 cm/min until failure. Multiple metrics are derived through this test. The yield strength (YS) of the material is defined as the transition from elastic to plastic deformation and is generally determined to be the stress near the end of the linear elastic region. The ultimate tensile strength (UTS) is the highest stress experienced by the sample during the test, and the elongation at break (EL) is the percent change in the length of the sample at the time of fracture. Izod impact testing was conducted according to ASTM F648-07. In this test, a standard sample of UHMWPE with two razor-sharp notches is broken by a swinging pendulum. The amount of energy required to break the sample is the Izod impact strength. Therefore, a sample that requires more energy to break has increased toughness and a higher Izod impact strength.

Typically, the ultimate tensile strength (UTS) of UHMWPE decreases with increasing crosslink density. Based upon this common correlation, the reduced UTS of Material C (Table 1) relative to Materials A and B suggests that higher levels of crosslinking have occurred in Material C.

TABLE 1

| Material | Yield Strength (MPa) | Ultimate Tensile Strength (MPa) | Elongation at Break (%) | Izod Impact Strength (kJ/m$^2$) |
|---|---|---|---|---|
| 500 ppm Vit E, 10 Mrad (Material A) | 23.7 ± 0.3 | 46.6 ± 2.1 | 280 ± 8 | 67 ± 1 |
| 500 ppm Curcumin, 10 Mrad (Material B) | 23.5 ± 0.3 | 44.4 ± 3.4 | 264 ± 13 | 65 ± 2 |
| 250 ppm Vit E + 250 ppm Curcumin, 10 Mrad (Material C) | 23.3 ± 0.4 | 42.8 ± 3.9 | 255 ± 20 | 66 ± 1 |
| 300 ppm Vit E + 300 ppm DPE, 10 Mrad (Material F) | 23.7 ± 0.7 | 38.2 ± 4.1 | 234 ± 22 | 69 ± 2 |
| 300 ppm Curcumin + 300 ppm DPE, 10 Mrad (Material G) | 23.7 ± 0.1 | 40.9 ± 2.3 | 232 ± 10 | 63 ± 2 |

Based upon these results, it is apparent that the addition of the curcumin to the Vit E/UHMWPE blend improves the oxidation resistance of the material while allowing for the reduction of the Vit E content. As a result, the irradiation dose necessary to obtain a given crosslink density and wear resistance in Material C could be decreased and result in additional improvements in the oxidation resistance. Alternatively, the irradiation dose could be maintained at 10 Mrad and result in both improved wear resistance and oxidation resistance compared to Material A.

Example 3

Neat GUR1020 UHMWPE resin was blended with the following:
- Material A—dl-alpha-tocopherol (vitamin E or Vit E) at a nominal concentration of 500 ppm (0.05 wt. %),
- Material F—dl-alpha-tocopherol and dipentaerythritol (DPE), a non-antioxidant polyhydric alcohol, at nominal concentrations of 300 ppm (0.03 wt. %) each.

These materials were then consolidated by compression-molding, annealed to relieve residual stresses, and subsequently gamma-irradiated with a nominal dose of 10 Mrad (100 kGy). Following irradiation, no heat treatments were conducted.

Again, two control materials were also evaluated. Neat GUR1020 UHMWPE was consolidated, annealed to relieve residual stresses and remained in the unirradiated condition (Material D—virgin). In addition, neat GUR1020 UHMWPE was consolidated, annealed to relieve residual stresses, gamma-irradiated with a nominal dose of 10 Mrad (100 kGy), and re-melted to stabilize the highly crosslinked material (Material E—10-XLPE). As in Example 2, the oxidation resistances of these materials were assessed through OIT experiments at hold temperatures of 190° C.

Figure 5:
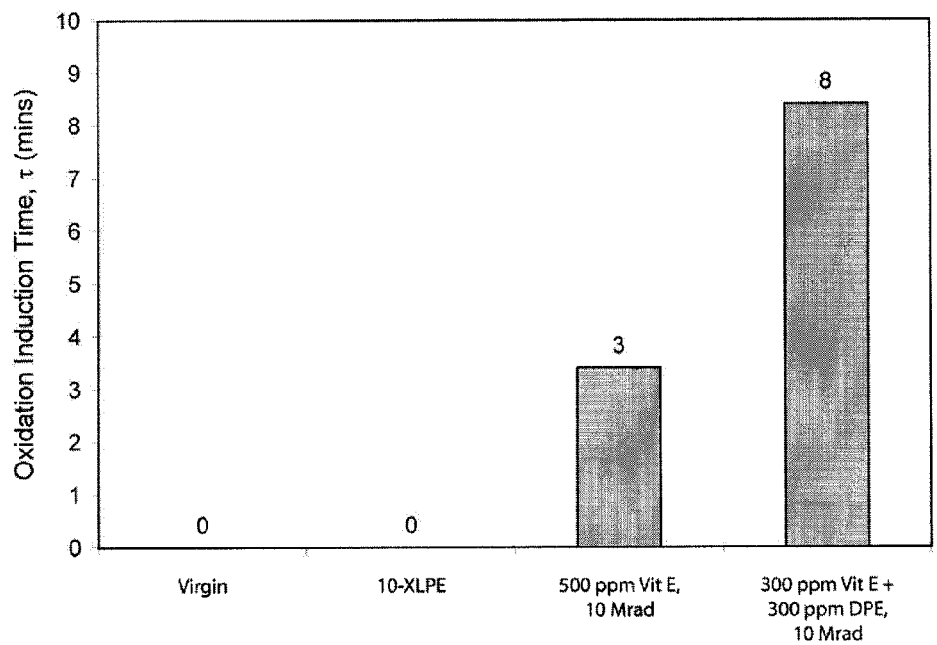
FIG. 5 shows the oxidation-induction-time (OIT) measurements for the samples of Example 3.

The standard control materials oxidized immediately upon initiation of the oxygen flow at 190° C. (FIG. 5), which results in an OIT of zero. UHMWPE blended with 500 ppm Vit E (Material A) resulted in an OIT of 3 mins (FIG. 5). The addition of 300 ppm DPE to a blend of UHMWPE with only 300 ppm Vit E (Material F) resulted in an OIT of 8 minutes, which represents an increase of 166%. Thus, the addition the second additive, DPE, with the Vit E improved the oxidation resistance while allowing the concentration of Vit E to be decreased by 40%, which will result in improved crosslinking efficiency. This improved oxidation resistance occurs despite the fact that DPE is not known to be an antioxidant and would, therefore, in theory exhibit an OIT of zero if combined with UHMWPE alone. The reduced ultimate tensile strength (UTS) of Material F relative to Material A suggests higher levels of crosslinking in Material F (Table 1). As a result, the irradiation dose necessary to obtain a given crosslink density and wear resistance could be decreased, which will also result in improved oxidation resistance and mechanical properties, particularly ductility and toughness, relative to Material A.

Alternatively, one could decrease the Vit E concentration further in the Vit E/DPE blend to provide improved wear resistance in combination with oxidation resistance equivalent to Material A.

Example 4

Neat GUR1020 UHMWPE resin was blended with the following.
- Material B—Purified curcumin, or diferuloymethane (97.7% by HPLC), at a nominal concentration of 500 ppm (0.05 wt. %),
- Material G—Purified curcumin, or diferuloymethane (97.7% by HPLC), and dipentaerythritol (DPE), a non-antioxidant polyhydric alcohol, at nominal concentrations of 300 ppm (0.03 wt. %) each.

These materials were then consolidated by compression-molding, annealed to relieve residual stresses, and subsequently gamma-irradiated with a nominal dose of 10 Mrad (100 kGy). Following irradiation, no heat treatments were conducted.

Again, two control materials were also evaluated. Neat GUR1020 UHMWPE was consolidated, annealed to relieve residual stresses and remained in the unirradiated condition (Material D—virgin). In addition, neat GUR1020 UHMWPE was consolidated, annealed to relieve residual stresses, gamma-irradiated with a nominal dose of 10 Mrad (100 kGy), and re-melted to stabilize the highly crosslinked material (Material E—10-XLPE). As in Example 2, the oxidation resistances of these materials were assessed through OIT experiments at hold temperatures of 190° C.

Figure 6:
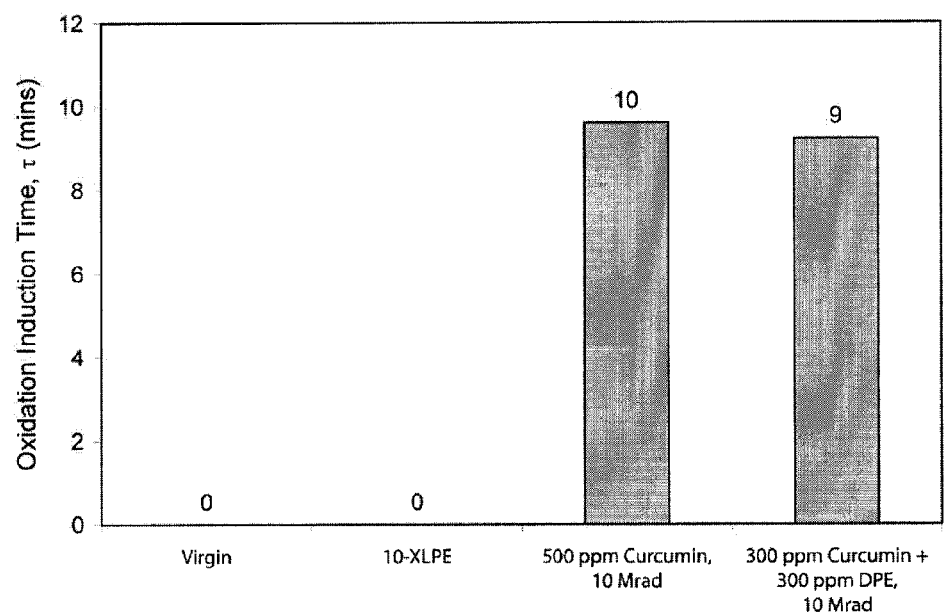
FIG. 6 shows the oxidation-induction-time (OIT) measurements for the samples of Example 4.

The standard control materials oxidized immediately upon initiation of the oxygen flow at 190° C. (FIG. 6), which results in an OIT of zero. Material B exhibited an OIT of 10 mins (FIG. 6). The addition of 300 ppm DPE to a blend of UHMWPE with only 300 ppm curcumin (Material G) resulted in oxidation resistance that is approximately equivalent to that of Material B. This improved oxidation resistance occurs despite the fact that DPE is not known to be an antioxidant and would, therefore, in theory exhibit an OIT of zero if combined with UHMWPE alone. The decrease in UTS for Material G (Table 1) suggests that a greater degree of crosslinking was obtained, which would result in improved wear resistance. Alternatively, one could irradiate the Material G with a lower gamma-radiation dose to achieve equivalent wear resistance, similar UTS and improved oxidation resistance relative to Material B.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Although the majority of examples described here are related to UHMWPE, any other polymer could be used. Thus, the breadth and scope of the present invention should not be limited by any of the above-described exemplary embodiments, but should be defined only in accordance with the following claims appended hereto and their equivalents.

REFERENCES

With the exception of the priority application (U.S. Provisional Patent Application No. 61/175,308, filed May 4, 2009, to which this application claims priority and which application is incorporated herein by reference in its entirety), the patents, patent applications, and publications mentioned in the specification are indicative of the levels of skill those of ordinary skill in the art to which the invention pertains. They are also intended to illustrate in a strictly non-limiting manner that which was known at the time of the invention to those of ordinary skill in the art to which the invention pertains. They are not intended to limit the invention described herein in any manner.

[1] L. Costa and P. Bracco, "Mechanisms of crosslinking, oxidative degradation and stabilization of UHMWPE," in *UHMWPE Biomaterials Handbook*, S. M. Kurtz, Ed., Burlington, Mass.: Elsevier, 2009.

[2] F. W. Shen, H. A. McKellop, and R. Salovey, "Irradiation of chemically crosslinked ultrahigh molecular weight polyethylene," J Polym Sci B, 1996; 34:1063-1077.

[3] M. Nakris, A. Tzur, A. Vaxman, H. G. Fritz, "Some properties of silane-grafted moisture-crosslinked polyethylene," Polym Eng Sci, 1985; 25(13):857-862.

[4] S. Al-Malaika and S. Issenhuth, "Processing effects on antioxidant transformation and solutions to the problem of antioxidant migration," in Polymer Durability: degradation, stabilization, and lifetime prediction, R. L. Clough, N. C. Billingham and K. T. Gillen, Eds., Washington D.C.: American Chemical Society, 1996.

[5] F. Gugumus, "Possibilities and limits of synergism with light stabilizers in polyolefins 1. HALS in polyolefins," Polym Degrad Stabil, 2002; 75(2):295-308.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Although the majority of examples described here are related to UHMWPE, any other polymer could be used. Thus, the breadth and scope of the present invention should not be limited by any of the above-described exemplary embodiments, but should be defined only in accordance with the following claims appended hereto and their equivalents.

Further, although the present invention and its advantages have been described in detail, it should be understood that various changes, substitutions and alterations can be made herein without departing from the invention as defined by the appended sentences and descriptions. Moreover, the scope of the present application is not intended to be limited to the particular embodiments of the process, machine, manufacture, composition of matter, means, methods, or steps presently existing or later to be developed that perform substantially the same function or achieve substantially the same result as the corresponding embodiments described herein may be utilized or wherein any differences are insubstantial. Accordingly, the appended statements are intended to include within their scope such processes, machines, manufacture, compositions of matter, means or steps.

What is claimed is:

1. A process for preparing crosslinked oxidation resistant UHMWPE for use in medical prostheses comprising the steps of: (i) obtaining UHMWPE resin; (ii) combining the UHMWPE resin with both a first amount of a first additive and a second amount of a second additive, wherein the first and the second additives are different additives; (iii) consolidating the UHMWPE that has been combined with the first and second additives; and (iv) crosslinking the consolidated UHMWPE to create oxidation resistant UHMWPE, wherein the first and second additives synergistically increase the oxidation resistance of the crosslinked UHMWPE.

2. The process of claim 1, wherein the obtained UHMWPE resin in step (i) has been crosslinked prior to the subsequent steps, including the crosslinking in step (iv).

3. The process of claim 1, wherein the crosslinking is selected from the group consisting of irradiation crosslinking and chemical crosslinking.

4. The process of claim 1, wherein the crosslinking is irradiation crosslinking.

5. The process of claim 1, wherein the amount of the first additive that is combined with the UHMWPE in step (ii) is about 50 ppm to about 5,000 ppm, and wherein the amount of the second additive that is combined with the UHMWPE in step (ii) is about 50 ppm to about 5,000 ppm.

6. The process of claim 1, wherein the amount of the first additive that is combined with the UHMWPE in step (ii) is about 0.005% to about 0.5%, and wherein the amount of the second additive that is combined with the UHMWPE in step (ii) is about 0.005% to about 0.5%.

7. The process of claim 4, wherein the dose of the crosslinking is about 1.5 MRad to about 30 MRad.

8. The process of claim 1, further comprising the step of machining the combined, consolidated, and crosslinked UHMWPE into a bearing component for a medical prosthesis.

9. The process of claim 8, wherein the crosslink densities of the combined, consolidated, crosslinked, and machined UHMWPE bearing component are about 0.03 mol/dm<3> to about 0.50 mol/dm<3>.

10. The process of claim 1, wherein the first additive is selected from the group consisting of phenolic antioxidants and hindered amines, and the second additive is selected from the group consisting of phosphorous additives, polyhydric alcohols, phenolic antioxidants, hindered amines, carotenoids, amino-acid-based additives, thiosynergists, and acid antioxidants.

11. The process of claim 10, wherein the phenolic antioxidants of the first additive are selected from the group consisting of tocopherols, tocotrienols, curcuminoids, flavonoids, phenylpropanoids, and synthetic phenolic antioxidants; the phosphorous additives of the second additive are selected from the group consisting of phosphites, phosphonites, and phosphines; the polyhydric alcohols of the second additive are selected from the group consisting of dipentaerythritol, tripentaerythritol, and trimethylolpropane ethoxylate; the phenolic antioxidants of the second additive are selected from the group consisting of tocopherols, tocotrienols, curcuminoids, flavonoids, phenylpropanoids synthetic antioxidants, and benzoquinols; the carotenoids of the second additive are selected from the group consisting of beta-carotene, lycopene, lutein, zeaxanthin, echinenone, and zeaxanthin; the amino-acid-based additives of the second additive are selected from the group consisting of glutathione, cystein, tyrosine, and tryptophan; and the acid antioxidants of the second additive are selected from the group consisting of ascorbyl palmitate, ascorbate, and lipoic acid.

12. The process of claim 11, wherein the tocopherols of the first additive are selected from the group consisting of dl-alpha-tocopherol, alpha-tocopherol, delta-tocopherol, gamma-tocopherol, and beta-tocopherol; the tocotrienols of the first additive are selected from the group consisting of alpha-tocotrienol, beta-tocotrienol, gamma-tocotrienol, and delta-tocotrienol; the curcuminoids of first additive are selected from the group consisting of curcumin, demethoxycurcumin, bisdemethoxycurcumin, tetrahydrocurcumin, hexahydrocurcumin, curcumin sulphate, curcumin-glucuronide, hexahydrocurcumin, and cyclocurcumin; the flavonoids of the first additive are selected from the group consisting of naringenin, quercetin, hesperitin, luteolin, catechins, anthocyanins; the phenylpropanoid of the first additive is eugenol; the phosphine of the second additive is pepfine; the tocopherols of the second additive are selected from the group consisting of dl-alpha-tocopherol, alpha-tocopherol, delta-tocopherol, gamma-tocopherol, and beta-tocopherol; the tocotrienols of the second additive are selected from the group consisting of alpha-tocotrienol, beta-tocotrienol, gamma-tocotrienol, and delta-tocotrienol; the curcuminoids of second additive are selected from the group consisting of curcumin, demethoxycurcumin, bisdemethoxycurcumin, tetrahydrocurcumin, hexahydrocurcumin, curcumin sulphate, curcumin-glucuronide, hexahydrocurcumin, and cyclocurcumin; the flavonoids of the second additive are selected from the group consisting of naringenin, quercetin, hesperitin, luteolin, catechins, and anthocyanins; and the benzoquinol of the second additive is selected from the group consisting of ubiquinol and coenzyme Q10.

13. The process of claim 12, wherein the catechins of the first additive are selected from the group consisting of epigallocatechin gallate, epigallocatechin, epicatechin gallate and epicatechin; the anthocyanins of the first additive are selected from the group consisting of cyanidin, delphinidin, malvidin, peonidin, petunidin, and pelargonidin; the catechins of the second additive are selected from the group consisting of epigallocatechin gallate, epigallocatechin, epicatechin gallate and epicatechin; and the anthocyanins of the second additive are selected from the group consisting of cyanidin, delphinidin, malvidin, peonidin, petunidin, and pelargonidin.

14. A process for preparing crosslinked oxidation resistant UHMWPE for use in medical prostheses comprising the steps of: (i) obtaining UHMWPE resin; (ii) combining the UHMWPE resin with both a first amount of a first additive and a second amount of a second additive, wherein the first and the second additives are different additives; (iii) consolidating the UHMWPE that has been combined with the first and second additives; and (iv) crosslinking the consolidated UHMWPE to create oxidation resistant UHMWPE, wherein the first and second additives synergistically increase the oxidation resistance of the crosslinked UHMWPE, wherein the first additive is a phenolic antioxidant and the second additive is a curcuminoid.

15. A process for preparing crosslinked oxidation resistant UHMWPE for use in medical prostheses comprising the steps of: (i) obtaining UHMWPE resin; (ii) combining the UHMWPE resin with both a first amount of a first additive and a second amount of a second additive, wherein the first and the second additives are different additives; (iii) consolidating the UHMWPE that has been combined with the first and second additives; and (iv) crosslinking the consolidated UHMWPE to create oxidation resistant UHMWPE, wherein the first and second additives synergistically increase the oxidation resistance of the crosslinked UHMWPE, wherein the first additive is dl-alpha-tocopherol and the second additive is curcumin.

16. The process of claim 15, wherein the first additive dl-alpha-tocopherol is combined with the UHMWPE in step (ii) at about 250 ppm; the second additive curcumin is combined with the UHMWPE in step (ii) at about 250 ppm; and the crosslinking in step (iv) is by irradiation at a dose of about 10 MRad.

17. A process for preparing crosslinked oxidation resistant UHMWPE for use in medical prostheses comprising the steps of: (i) obtaining UHMWPE resin; (ii) combining the UHMWPE resin with both a first amount of a first additive and a second amount of a second additive, wherein the first and the second additives are different additives; (iii) consolidating the UHMWPE that has been combined with the first and second additives; and (iv) crosslinking the consolidated UHMWPE to create oxidation resistant UHMWPE, wherein the first and second additives synergistically increase the oxidation resistance of the crosslinked UHMWPE, wherein the first additive is dl-alpha-tocopherol and the second additive is dipentaerythritol.

18. The process of claim 17, wherein the first additive dl-alpha-tocopherol is combined with the UHMWPE in step (ii) at about 300 ppm; the second additive dipentaerythritol is combined with the UHMWPE in step (ii) at about 300 ppm; and the crosslinking in step (iv) is by irradiation at a dose of about 10 MRad.

19. A process for preparing crosslinked oxidation resistant UHMWPE for use in medical prostheses comprising the steps of: (i) obtaining UHMWPE resin; (ii) combining the UHMWPE resin with both a first amount of a first additive and a second amount of a second additive, wherein the first and the second additives are different additives; (iii) consolidating the UHMWPE that has been combined with the first and second additives; and (iv) crosslinking the consolidated UHMWPE to create oxidation resistant UHMWPE, wherein the first and second additives synergistically increase the oxidation resistance of the crosslinked UHMWPE, wherein the first additive is curcumin and the second additive is dipentaerythritol.

20. The process of claim 19, wherein the first additive curcumin is combined with the UHMWPE in step (ii) at about 300 ppm; the second additive dipentaerythritol is combined with the UHMWPE in step (ii) at about 300 ppm; and the crosslinking in step (iv) is by irradiation at a dose of about 10 MRad.

21. A medical prosthesis comprising a bearing component comprising crosslinked UHMWPE made by the process of claim 1.

22. The medical prosthesis of claim 21, wherein the first additive is selected from the group consisting of phenolic antioxidants and hindered amines, and the second additive is selected from the group consisting of phosphorous additives, polyhydric alcohols, phenolic antioxidants, hindered amines, carotenoids, amino-acid-based additives, thiosynergists, and acid antioxidants.

23. The medical prosthesis of claim 22, wherein the phenolic antioxidants of the first additive are selected from the group consisting of tocopherols, tocotrienols, curcuminoids, flavonoids, phenylpropanoids, and synthetic phenolic antioxidants; the phosphorous additives of the second additive are selected from the group consisting of phosphites, phosphonites, and phosphines; the polyhydric alcohols of the second additive are selected from the group consisting of dipentaerythritol, tripentaerythritol, and trimethylolpropane ethoxylate; the phenolic antioxidants of the second additive are selected from the group consisting of tocopherols, tocotrienols, curcuminoids, flavonoids, phenylpropanoids synthetic antioxidants, and benzoquinols; the carotenoids of the second additive are selected from the group consisting of beta-carotene, lycopene, lutein, zeaxanthin, echinenone, and zeaxanthin; the amino-acid-based additives of the second additive are selected from the group consisting of glutathione, cystein, tyrosine, and tryptophan; and the acid antioxidants of the second additive are selected from the group consisting of ascorbyl palmitate, ascorbate, and lipoic acid.

24. The medical prosthesis of claim 21, wherein the medical prosthesis is a joint prosthesis.

25. The medical prosthesis of claim 24, wherein the medical prosthesis is a hip or a knee joint prosthesis.

26. A medical prosthesis comprising a bearing component comprising crosslinked UHMWPE made by the process of claim 15.

27. A medical prosthesis comprising a bearing component comprising crosslinked UHMWPE made by the process of claim 17.

28. A medical prosthesis comprising a bearing component comprising crosslinked UHMWPE made by the process of claim 19.

29. A medical prosthesis comprising a bearing component comprising crosslinked UHMWPE made by the process of claim 14.

* * * * *